(12) United States Patent
Huang et al.

(10) Patent No.: US 10,131,620 B2
(45) Date of Patent: Nov. 20, 2018

(54) PROCESS FOR PRODUCING DIMETHYL CARBONATE

(71) Applicant: Chang Chun Plastics Co. Ltd., Taipei (TW)

(72) Inventors: Chien Fu Huang, Taipei (TW); Yi Ta Tsai, Taipei (TW)

(73) Assignee: CHANG CHUN PLASTICS CO., LTD., Taipei (TW)

( * ) Notice: Subject to any disclaimer, the term of this patent is extended or adjusted under 35 U.S.C. 154(b) by 0 days.

(21) Appl. No.: 15/285,024

(22) Filed: Oct. 4, 2016

(65) Prior Publication Data

US 2017/0107170 A1    Apr. 20, 2017

Related U.S. Application Data

(63) Continuation-in-part of application No. 14/918,015, filed on Oct. 20, 2015, now Pat. No. 9,656,943.

(51) Int. Cl.
| | |
|---|---|
| *C07C 43/00* | (2006.01) |
| *C07C 69/96* | (2006.01) |
| *C07C 29/60* | (2006.01) |
| *C07C 29/62* | (2006.01) |
| *C07C 68/06* | (2006.01) |
| *C07C 29/128* | (2006.01) |

(52) U.S. Cl.
CPC ............ *C07C 69/96* (2013.01); *C07C 29/128* (2013.01); *C07C 29/60* (2013.01); *C07C 29/62* (2013.01); *C07C 68/065* (2013.01)

(58) Field of Classification Search
None
See application file for complete search history.

(56) References Cited

U.S. PATENT DOCUMENTS

| | | |
|---|---|---|
| 2,667,497 A | 1/1954 | Cline |
| 2,993,908 A | 7/1961 | Millikan et al. |
| 3,457,282 A | 7/1969 | Polak et al. |
| 4,181,676 A | 1/1980 | Buysch et al. |
| 4,661,609 A | 4/1987 | Knifton |
| 4,691,041 A | 9/1987 | Duranleau et al. |
| 4,734,518 A | 3/1988 | Knifton |
| 4,841,072 A | 6/1989 | Harvey |
| 4,931,571 A | 6/1990 | Weinstein |
| 5,231,212 A | 7/1993 | Buysch et al. |
| 5,359,094 A | 10/1994 | Teles et al. |
| 7,605,285 B2 | 10/2009 | Kobayashi et al. |
| 8,809,569 B2 | 8/2014 | Zhang et al. |
| 9,006,498 B2 | 4/2015 | Ten Kate et al. |
| 9,051,424 B2 | 6/2015 | Lobert et al. |
| 2004/0162226 A1 | 8/2004 | Sunder et al. |
| 2005/0075258 A1 | 4/2005 | Kessler et al. |
| 2005/0113271 A1 | 5/2005 | Pegelow et al. |
| 2009/0270588 A1* | 10/2009 | Krafft ................. C07C 29/62 528/421 |
| 2009/0270657 A1 | 10/2009 | Van Der Heide |
| 2011/0196167 A1 | 8/2011 | Almusaiteer et al. |
| 2012/0264941 A1 | 10/2012 | Jerome et al. |
| 2013/0165669 A1 | 6/2013 | Zhao et al. |
| 2015/0152079 A1 | 6/2015 | Mignani et al. |
| 2015/0239858 A1 | 8/2015 | Lee et al. |

FOREIGN PATENT DOCUMENTS

| | | |
|---|---|---|
| CN | 1049212 C | 2/2000 |
| CN | 1074310 C | 11/2001 |
| CN | 1138736 C | 2/2004 |
| CN | 1235864 C | 1/2006 |
| CN | 1241900 C | 2/2006 |
| CN | 100364956 C | 1/2008 |
| CN | 100453540 C | 1/2009 |
| CN | 1946660 B | 11/2012 |
| WO | WO-2009016149 A2 | 2/2009 |
| WO | WO-2011157551 A1 | 12/2011 |

OTHER PUBLICATIONS

Sankar et al. Applied Catalysis A: General 312, 2006, 108-114.*
Wang et al. Journal of Molecular Catalysis A: Chemical 249, 2006, 143-148.*
Zhang et al. Shiyou Huagong, 2007, 36(3), 282-284 (abstract provided).*
Sun et al. Xiandai Huagong (2011), 31(5), 53-55.
Giani et al. Computers and Chemical Engineering 29 (2005) 1661-1676.

* cited by examiner

*Primary Examiner* — Ana Z Muresan
(74) *Attorney, Agent, or Firm* — Nixon Peabody LLP; Thomas P. Pavelko

(57) ABSTRACT

The present disclosure relates to a recycling method for producing dimethyl carbonate and dimethyl carbonate derivatives. The process is unique in that it produces a by-product that can be re-used in the process as a raw material for repeating the process. For example, when the process is directed to synthesizing dimethyl carbonate, glycerol is used as a starting material. Glycerol is also a by-product produced during formation of dimethyl carbonate, and therefore it can be re-used as starting material to generate more dimethyl carbonate.

18 Claims, 1 Drawing Sheet

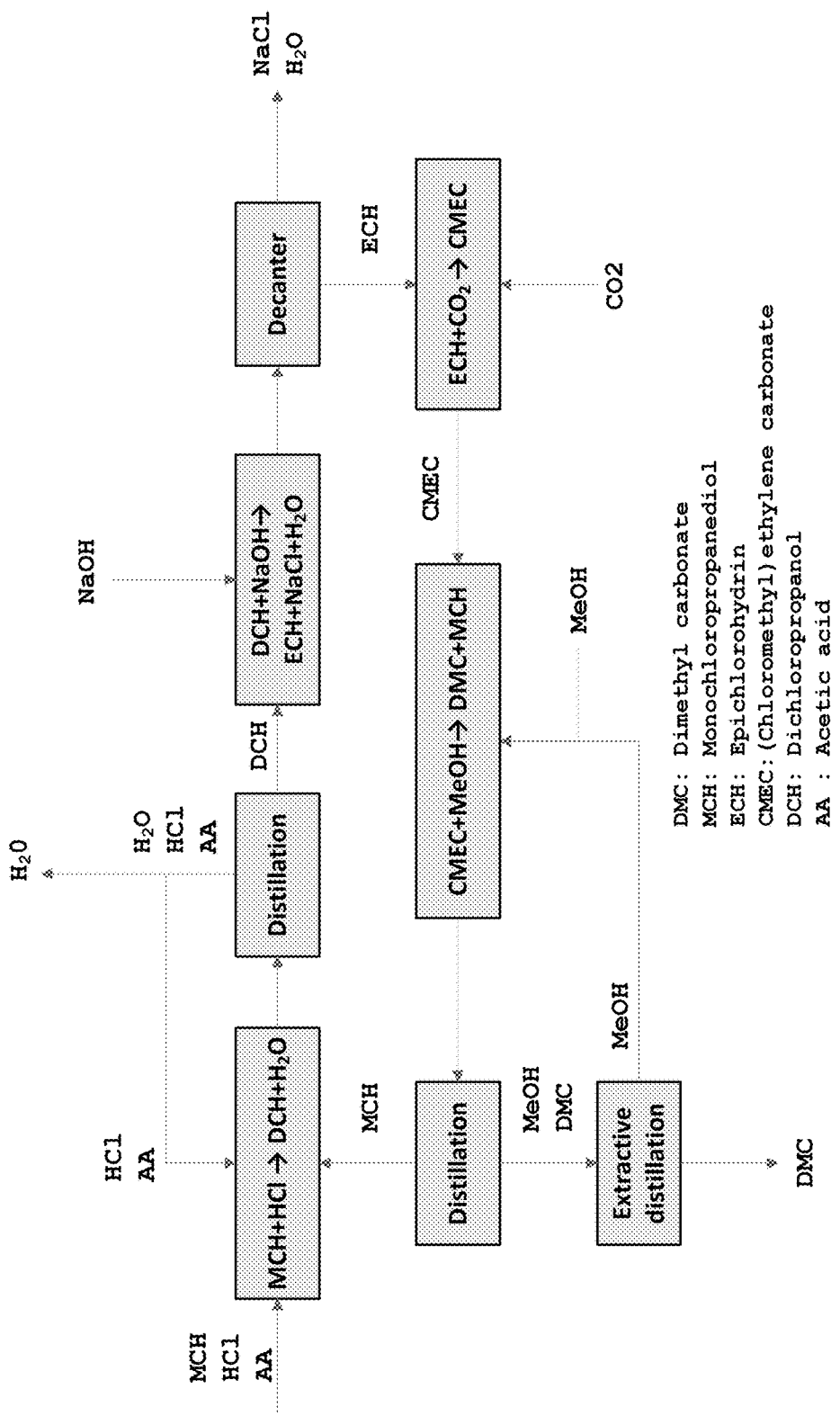

PROCESS FOR PRODUCING DIMETHYL CARBONATE

CROSS REFERENCE TO RELATED APPLICATIONS

This application is a Continuation-in-Part of U.S. application Ser. No. 14/918,015, filed Oct. 20, 2015, the entire content of which is fully incorporated herein by reference.

FIELD OF THE DISCLOSURE

The present disclosure relates to a method for producing dimethyl carbonate and dimethyl carbonate derivatives. The process is unique in that it produces a by-product that can be re-used in the process as a raw material for repeating the process.

BACKGROUND

Dimethyl carbonate (DMC) is an organic compound with the formula $OC(OCH_3)_2$. It is a colorless, flammable liquid. It is classified as a carbonate ester. It is useful as a methylating agent and as a solvent that is exempt from classification as a volatile organic compound (VOC) in the United States. Dimethyl carbonate is often considered to be a green reagent by minimizing the use and generation of hazardous substances. Dimethyl carbonate's main benefit over other methylating reagents such as iodomethane and dimethyl sulfate is its much lower toxicity and its biodegradability.

DMC has grown in popularity and applications as a replacement for methyl ethyl ketone, tert-butyl acetate, and parachlorobenzotrifluoride. It has an ester or alcohol like odor, which is more favorable to users than most hydrocarbon solvents it replaces. DMC has an evaporation rate of 3.22 (butyl acetate=1.0), which slightly slower than methyl ethyl ketone (MEK) (3.8) and ethyl acetate (4.1) and faster than toluene (2.0) and isopropanol (1.7). It has solubility profile similar to common glycol ethers, meaning DMC can solve most common coating resins. Hildebrand solubility parameter is 20.3 Mpa and Hansen solubility parameters are: dispersion=15.5, polar=3.9, H bonding=9.7. DMC is partially soluble in water up to 13%, however DMC has hydrolyzed in water based systems over time to methanol and $CO_2$ unless properly buffered. DMC is a flammable liquid that has a flash point of 17° C. (63° F.) making it safer than acetone, methyl acetate and methyl ethyl ketone from a flammability point of view.

SUMMARY OF THE DISCLOSURE

The present disclosure relates to a method for producing dimethyl carbonate (DMC) and dimethyl carbonate derivatives (compounds of Formula (VI)). The process is unique in that it produces a by-product that can be re-used in the process as a raw material for repeating the process. When the product of interest is dimethyl carbonate, for example, the by-product is 3-chloropropane-1,2-diol can be recycled back into the process as a starting material. The process is additionally unique in that it does not produce ethylene glycol or propylene glycol as by-products. Traditional processes for producing compounds such as dimethyl carbonate involve reacting an oxirane compound with carbon dioxide, which results in the formation of ethylene glycol and propylene glycol as by-products.

In general, the instant disclosure relates to a process for producing a compound of Formula (VI) comprising:

(a) reacting a compound of Formula (I) with an halogenating agent to form a compound of Formula (II)

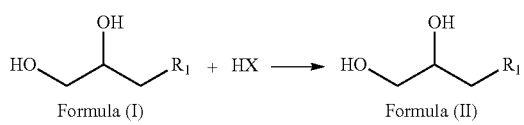

wherein, X is F, Cl, Br, or I; and $R_1$ is a halide, hydrogen, hydroxyl, $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups;

(b) reacting the compound of Formula (II) with a base to form a compound of Formula (III)

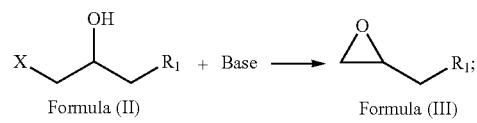

(c) reacting the compound of Formula (III) with carbon dioxide to form a compound of Formula (IV)

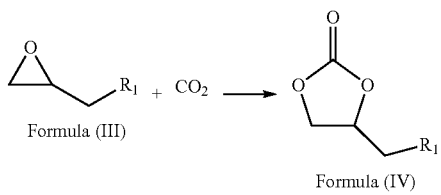

wherein, $R_1$ is a halide, hydrogen, hydroxyl, $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups; and (d) reacting the compound of Formula (IV) with an alcohol to form a compound of Formula (VI) and the compound of Formula (I)

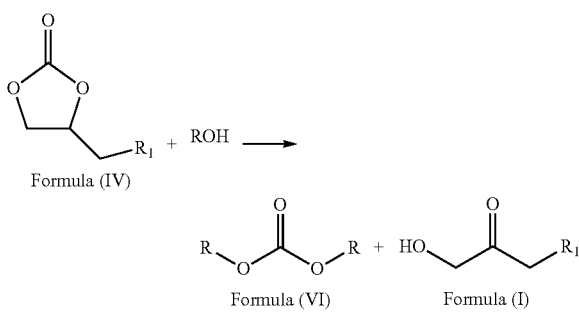

wherein, R is a $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups.

The instant disclosure also relates to a method for producing dimethyl carbonate. The method typically comprises:
(a) reacting 3-chloropropane-1,2-diol with hydrochloric acid to form 1,3-dichloro-2-propanol and water

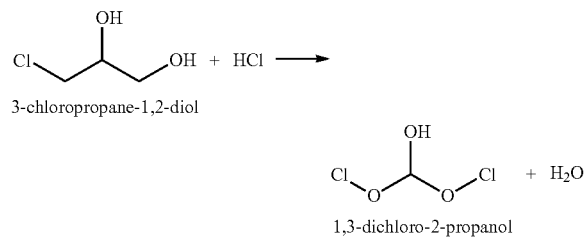

(b) reacting 1,3-dichloro-2-propanol with sodium hydroxide to form epichlorohydrin, sodium chloride, and water

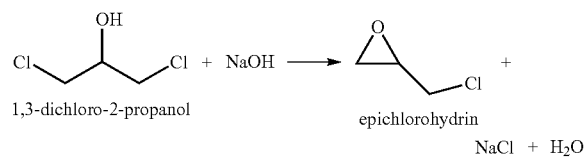

(c) reacting epichlorohydrin with carbon dioxide in the presence of tetrapropylammonium bromide(TPAB) to form (chloromethyl)ethylene carbonate

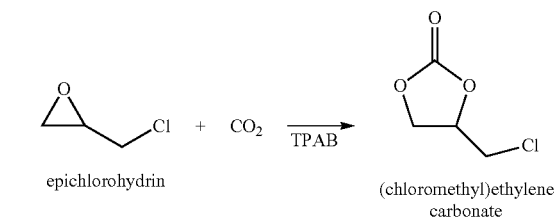

(d) reacting the (chloromethyl)ethylene carbonate with methanol in the presence of tetrabutyl titanate (TBT) to form dimethyl carbonates and 3-chloropropane-1,2-diol, and

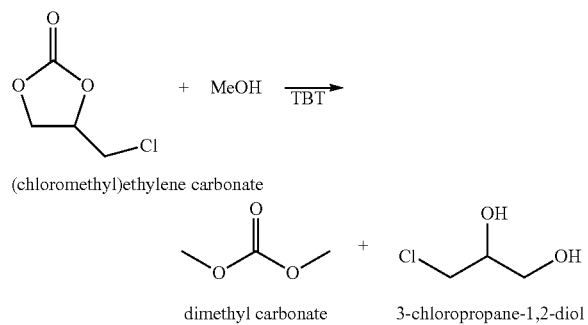

(e) recycling the 3-chloropropane-1,2-diol formed in (d) into (a).

BRIEF DESCRIPTION OF THE DRAWINGS

Implementations of the present technology will now be described, by way of example only, with reference to the attached figures, wherein:

FIG. 1 is a schematic illustrating various steps that can be included in the instant process.

It should be understood that the various aspects are not limited to the arrangements and instrumentality shown in the drawings.

DETAILED DESCRIPTION OF THE DISCLOSURE

The instant disclosure relates to a process for producing a compound of Formula (VI) comprising:
(a) reacting a compound of Formula (I) with an halogenating agent to form a compound of Formula (II)

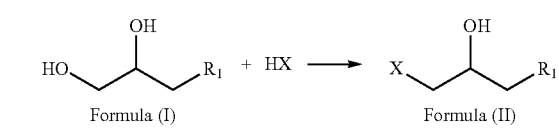

wherein, X is F, Cl, Br, or I; and $R_1$ is a halide, hydrogen, hydroxyl, $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups;
(b) reacting the compound of Formula (II) with a base to form a compound of Formula (III)

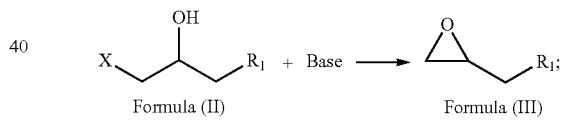

(c) reacting the compound of Formula (III) with carbon dioxide to form a compound of Formula (IV)

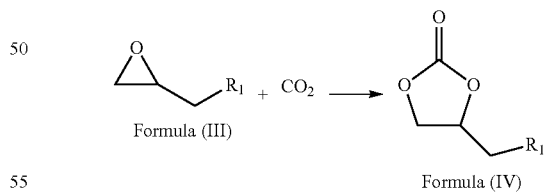

wherein, $R_1$ is a halide, hydrogen, hydroxyl, $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups; and
(d) reacting the compound of Formula (IV) with an alcohol to form a compound of Formula (VI) and the compound of Formula (I)

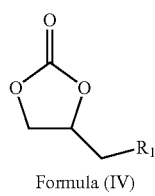 + ROH ⟶

Formula (IV)

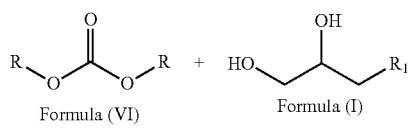

Formula (VI)    Formula (I)

wherein, R is a $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups.

The halogenating agent in (a) may be hydrogen chloride or a mixture of gaseous hydrogen chloride and an aqueous solution of hydrogen chloride. Also, the reaction of the compound of Formula (I) with the halogenating agent in (a) can be carried out in the presence of a catalyst. The catalyst may be, for example, an organic acid catalyst, and inorganic acid catalyst, or a heterogeneous acid catalyst. In some cases, the catalyst is an organic acid catalyst selected from the group consisting of a carboxylic, a sulfonic, and a phosphoric acid. In other cases, the catalyst is an organic catalyst such as acetic acid.

The base in (b) can be a hydroxide, a carbonate and a bicarbonate of alkali metal or an alkaline earth metal. In some cases, for example the base in (b) is selected from the group consisting of LiOH, NaOH, KOH, CsOH, RbOH, $Mg(OH)_2$, $Ca(OH)_2$, $Sr(OH)_2$, $NH_4OH$, $Ba(OH)_2$, $Na_2CO_3$, $K_2CO_3$, $NaHCO_3$, $KHCO_3$, and basic ion exchange resin. In other cases, the base is NaOH. Furthermore, the reaction of the compound of Formula (II) with a base to form a compound of Formula (III) in (b) may be carried out in a solvent. In some cases, the solvent is water.

Examples of basic ion exchange resins are provided in the table 1 below.

TABLE 1

| Grade name | Chemical structure or Functional group |
|---|---|
| DIAION PA312 | —CH₂—CH— (phenyl)-CH₂N⁺(CH₃)₃Cl⁻ |
| DIAION PA316 | —CH₂—CH— (phenyl)-CH₂N⁺(CH₃)₃Cl⁻ |

TABLE 1-continued

| Grade name | Chemical structure or Functional group |
|---|---|
| AMBERLITE UP900 | Trimethyl ammonium |
| Purolite A500Plus | Type I Quaternary Ammonium |
| DIAION WA20 | —CH₂—CH— (phenyl)-CH₂NH(CH₂CH₂NH)nH |

The reaction of the compound of Formula (III) with carbon dioxide in (c) is often carried out in the presence of a catalyst, such as an alkali metal halide salt or quaternary ammonium halide. Alkali metal halide salts include, for example, NaCl, NaBr, NaI, KCl, KBr and KI. Quaternary ammonium halides include, for example, tetraethylammonium bromide, tetrapropylammonium bromide, tetraethylammonium chloride and tetraethylammonium iodide.

The reaction of the compound of Formula (IV) with alcohol in (d) is also often carried out in the presence of a catalyst. Useful catalysts include, for example, a quadrivalent organotitanium compound having the formula $Ti(OR)_4$, or a quadrivalent organozirconium compound having the formula $Zr(OR)_4$, wherein, R is a $C_1$-$C_8$ alkyl, and $C_6$-$C_{10}$ aryl group. In other cases, the catalyst is tetrabutyl titanate.

The instant disclosure also relates specifically to a process for producing dimethyl carbonate, the process comprising:

(a) reacting 3-chloropropane-1,2-diol with a hydrogen halide to form a compound of Formula (II-a);

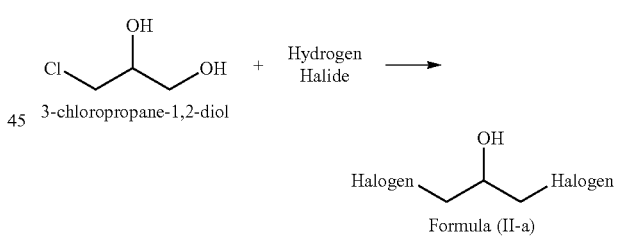

3-chloropropane-1,2-diol

Formula (II-a)

(b) reacting the compound of Formula (II-a) with a base to form epichlorohydrin,

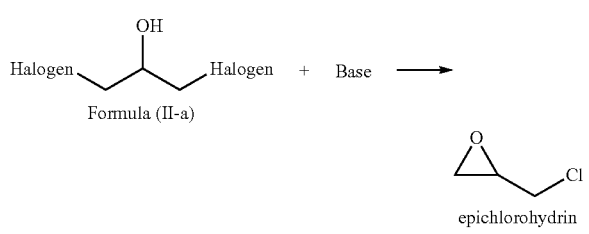

Formula (II-a)

epichlorohydrin (c) reacting the epichlorohydrin with carbon dioxide to form (chloromethyl)ethylene carbonate; and

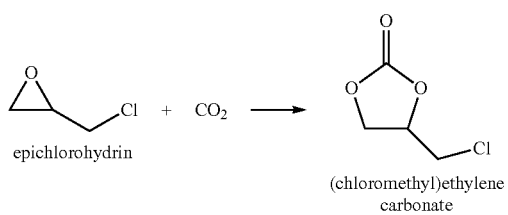
epichlorohydrin
(chloromethyl)ethylene carbonate (d) reacting the (chloromethyl)ethylene carbonate with methanol to form dimethyl carbonate and 3-chloropropane-1,2-diol

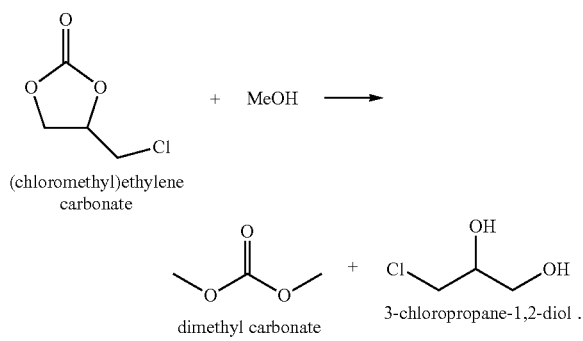
(chloromethyl)ethylene carbonate dimethyl carbonate    3-chloropropane-1,2-diol.

The hydrogen halide in (a) may be, for example, HCl and the compound of Formula (II-a) may be, for example, 1,3-dichloro-2-propanol. Furthermore, the reaction of 3-chloropropane-1,2-diol with the hydrogen halide in (a) may be carried out in the presence of a catalyst. The catalyst may be an organic acid catalyst, an inorganic acid catalyst, or a heterogeneous acid catalyst. In some cases, the catalyst is an organic acid catalyst selected from the group consisting of a carboxylic, a sulfonic, and a phosphoric acid. In other cases, the organic acid catalyst is acetic acid.

The base in (b) may be, for example, a hydroxide, a carbonate and a bicarbonate of alkali metal and alkaline earth metal. In some cases, the base in (b) is selected from the group consisting of LiOH, NaOH, KOH, CsOH, RbOH, $Mg(OH)_2$, $Ca(OH)_2$, $Sr(OH)_2$, NH4OH, $Ba(OH)2$, $Na_2CO_3$, and $K_2CO_3$, $NaHCO_3$ $KHCO_3$, and a basic ion exchange resin. In other cases, the base is NaOH. The reaction of the compound of Formula (II) with a base to form a compound of Formula (III) in (b) can be carried out in a solvent. In some cases, the solvent is water.

The reaction of epichlorohydrin with carbon dioxide in (c) can be carried out in the presence of a catalyst. For example, the catalyst may be an alkali metal halide salt, or quaternary ammonium halide. Examples of alkali metal halide salts include, but are not limited to, NaCl, NaBr, NaI, KCl, KBr, and KI. Quaternary ammonium halide include, but are not limited to, tetraethylammonium bromide, tetrapropylammonium bromide, tetraethylammonium chloride, and tetraethylammonium iodide.

The reaction of the compound of Formula (IV) with methanol in (d) can be carried out in the presence of a catalyst. The catalyst may be, for example, a quadrivalent organotitanium compound having the formula $Ti(OR)_4$, or a quadrivalent organozirconium compound having the formula $Zr(OR)_4$, wherein, R is a $C_1$-$C_8$ alkyl, and $C_6$-$C_{10}$ aryl group. In other cases, the catalyst is tetrabutyl titanate.

The instant disclosure further relates to a method for producing dimethyl carbonate comprising:
(a) reacting 3-chloropropane-1,2-diol with hydrochloric acid to form 1,3-dichloro-2-propanol and water

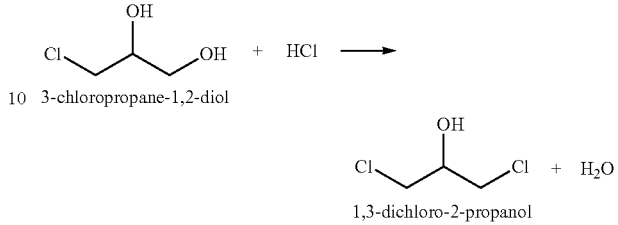
3-chloropropane-1,2-diol 1,3-dichloro-2-propanol (b) reacting 1,3-dichloro-2-propanol with sodium hydroxide to form epichlorohydrin, sodium chloride, and water

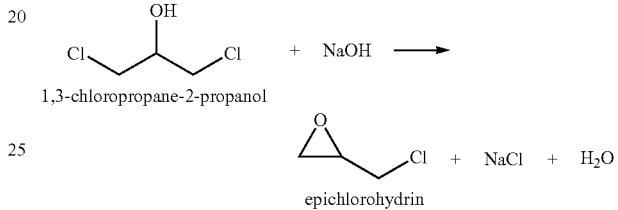
1,3-chloropropane-2-propanol epichlorohydrin (c) reacting epichlorohydrin with carbon dioxide in the presence of tetrapropylammonium bromide(TPAB) to form (chloromethyl)ethylene carbonate

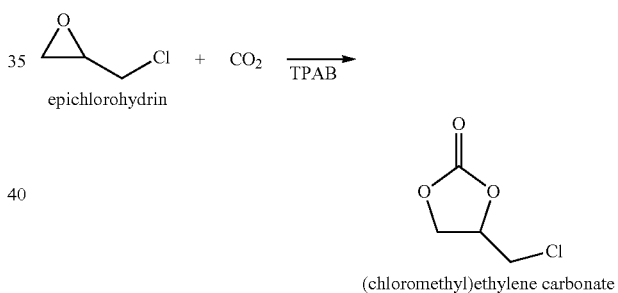
epichlorohydrin (chloromethyl)ethylene carbonate (d) reacting the (chloromethyl)ethylene carbonate with methanol in the presence of tetrabutyl titanate (TBT) to form dimethyl carbonates and 3-chloropropane-1,2-diol, and

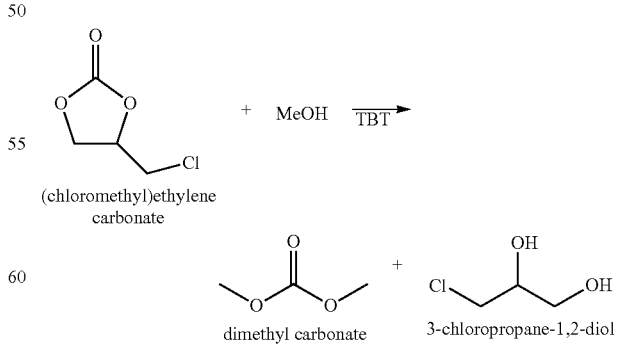
(chloromethyl)ethylene carbonate dimethyl carbonate    3-chloropropane-1,2-diol (e) recycling the 3-chloropropane-1,2-diol formed in (d) into (a).

In some cases the reaction of the 3-chloropropane-1,2-diol with hydrochloric acid in (a) is carried out in the presence of a catalyst, such as, for example, an organic acid catalyst selected from the group consisting of carboxylic, sulfonic, and phosphoric acids. In other cases, the organic acid catalyst is acetic acid. Finally, the water and sodium chloride produced in (a) and/or (b) can be removed by decanter and distillation

EXAMPLE 1

A 3-chloropropane-1,2-diol (129.33 g), acetic acid (42.26 g), and 37% hydrogen chloride solution (461.36 g) was placed in a 1 liter glass reactor, and then stirred using an agitator. The solution was heating to 120° C. for 2 hours at 4.5 atm pressure. The product was analysed by GC, and the conversion of 3-chloropropane-1,2-diol was 93.6%, and the selectivity of 1,3-dichloro-2-propanol was 93.18%, and the selectivity of 2,3-dichloro-1-propanol was 2.26%.

1,3-dichloro-2-propanol (11.77 g), and 20% NaOH(18.24 g) were placed in a 50 ml sample bottle, and stirred with a teflon stir bar. The solution was cooling to 20° C. for 30 min at 1 atm pressure. The product was analysed by GC, and the conversion of 1,3-dichloro-2-propanol was 99.2%, and the selectivity of epichlorohydrin was 95%.

Tetrapropylammonium bromide was used to catalyze the reaction of epichlorohydrin to (chloromethyl)ethylene carbonate using carbon dioxide. Epichlorohydrin (320.32 g) and tetrapropylammonium bromide (9.2 g) were charged to the 400 mL stainless steel autoclave, and then the autoclave was filled with carbon dioxide. At room temperature the carbon dioxide was added to bring the initial pressure to 30 atm and the reaction was begun by heating to 100° C. Carbon dioxide was continually added to the autoclave to maintain this pressure. After a 4 hour reaction period, the reactor was cooled and vented, and the product was recovered. The results are presented in the table 2 below (Inventive Example 1) and contrasted with a comparative example from U.S. Pat. No. 4,931,571, which describes the formation of ethylene carbonate from ethylene oxide.

tetrapropylammonium bromide (0.12 g) were charged to the 400 mL stainless steel autoclave, and then the autoclave was filled with carbon dioxide. At room temperature the carbon dioxide was added to bring the initial pressure to 30 atm and the reaction was begun by heating 100° C. Carbon dioxide was continually added to the autoclave to maintain this pressure. After a 19.5 hour reaction period, the reactor was cooled and vented, and the product was recovered. The product was analysed by GC, and the conversion of epichlorohydrin was 97.11%, and the selectivity of (chloromethyl) ethylene carbonate was 99.82%.

EXAMPLE 3

Tetrapropylammonium bromide was used to catalyze the reaction of epichlorohydrin to (chloromethyl)ethylene carbonate using carbon dioxide. Epichlorohydrin (80.15 g) and tetrapropylammonium bromide (2.3 g) were charged to the 400 mL stainless steel autoclave, and then the autoclave was filled with carbon dioxide. At room temperature the carbon dioxide was added to bring the initial pressure to 30 atm and the reaction was begun by heating to 100° C. Carbon dioxide was continually added to the autoclave to maintain this pressure. After an 8 hour reaction period, the reactor was cooled and vented, and the product was recovered. The product was analyzed by GC, and the conversion of epichlorohydrin was 99.46%, and the selectivity of (chloromethyl) ethylene carbonate was 99.81%.

EXAMPLE 4

(Chloromethyl)ethylene carbonate (20.11 g), methanol (47.03 g), and tetrabutyl titanate (0.1 g) were placed in a 150 mL stainless steel autoclave, and then the autoclave was filled with nitrogen to 10 kg/cm² G at room temperature. The reaction was begun by heating to 150° C., and this temperature was maintained for 1 hour. The reaction pressure was 15 kg/cm² (increased with temperature, 30° C.→150° C., 10 kg/cm²→24 kg/cm²). The product was analyzed by GC. The

TABLE 2

| | Charge | Temp (° C.) | Pressure (bar) | Time (hour) | Converstion (%) | Selectivity (%) |
|---|---|---|---|---|---|---|
| Inventive Example 1 | 3.46 mol (epichlorohydrin) | 100 | 30 | 4 | 99.4 (epichlorohydrin) | 98.5 chloromethyl-ethylene carbonate) |
| Comparative Example U.S. Pat. No. 4,931,571 | 2.22 mol (ethylene oxide) | 150 | 42.4 | 2 | 84.8 (ethylene oxide) | 91.4 (ethylene carbonate) |

(Chloromethyl)ethylene carbonate (20.17 g), methanol (46.90 g), and tetrabutyl titanate (1.0 g) were placed in a 150 mL stainless steel autoclave, and then the autoclave was filled with nitrogen to 10 kg/cm² G at room temperature. The reaction was begun by heating to 150° C., and this temperature was maintained for 1 hours. The reaction pressure was 15 kg/cm² (increased with temperature, 30° C.→150° C., 10 kg/cm²→24 kg/cm²). The product was analyzed by GC. The conversion of (chloromethyl) ethylene carbonate was 74.8%, and the selectivity of dimethyl carbonate was 84.1%, and the selectivity of 3-chloropropane-1,2-diol was 84.6%.

EXAMPLE 2

Tetrapropylammonium bromide was used to catalyze the reaction of epichlorohydrin to (chloromethyl)ethylene carbonate using carbon dioxide. Epichlorohydrin (40.06 g) and conversion of (chloromethyl) ethylene carbonate was 52.5%, and the selectivity of dimethyl carbonate was 76.5%, and the selectivity of 3-chloropropane-1,2-diol was 78.6%.

EXAMPLE 5

(Chloromethyl)ethylene carbonate (26.03 g), methanol (36.59 g), and tetrabutyl titanate (1.0 g) were placed in a 150 mL stainless steel autoclave, and then the autoclave was filled with nitrogen to 10 kg/cm² G at room temperature. The reaction was begun by heating to 150° C., and this temperature was maintained for 1 hours. The reaction pressure was 15 kg/cm² (increased with temperature, 30° C.→150° C., 10 kg/cm²→24 kg/cm²). The product was analyzed by GC. The conversion of (chloromethyl) ethylene carbonate was 65.3%, and the selectivity of dimethyl carbonate was 80.9%, and the selectivity of 3-chloropropane-1,2-diol was 83.3%.

The invention claimed is:

1. A process for producing a compound of Formula (VI) the process comprising:
   (a) reacting a compound of Formula (I) with an halogenating agent of formula HX to form a compound of Formula (II)

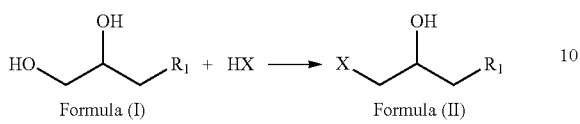

wherein,
   X is F, Cl, Br, or I; and
   R1 is a halide, hydrogen, hydroxyl, $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups;
   (b) reacting the compound of Formula (II) with a base in water to form a compound of Formula (III)

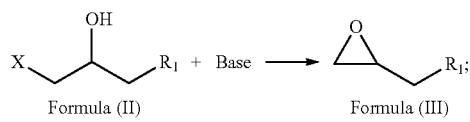

(c) reacting the compound of Formula (III) with carbon dioxide to form a compound of Formula (IV)

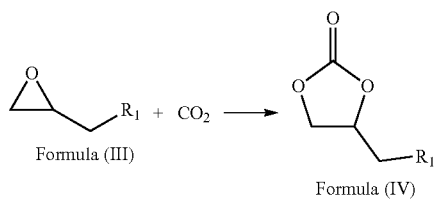

wherein,
   R1 is a halide, hydrogen, hydroxyl, $C_1$-$C_8$ alkyl, $C_1$-$C_8$ alkenyl, $C_1$-$C_8$ alkoxy, $C_1$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups; and
   (d) reacting the compound of Formula (IV) with an alcohol of formula ROH in the presence of a catalyst comprising tetrabutyl titanate (TBT) to form a compound of Formula (VI) and the compound of Formula (I)

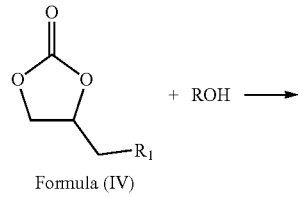

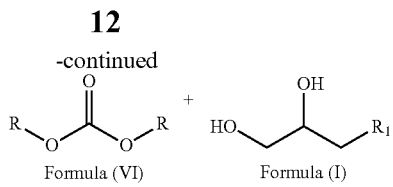

wherein,
   R is a $C_1$-$C_8$ alkyl, $C_1$-$C_8$ alkenyl, $C_1$-$C_8$ alkoxy, $C_3$-$C_8$ cycloalkyl, $C_6$-$C_{10}$ aryl group or a 5-10 member heteroaryl group having 1-3 heteroatoms selected from the group consisting of N, O and S, wherein the alkyl, alkenyl, cycloalkyl, aryl group and heteroaryl group can optionally be substituted by one or more hydroxyl groups.

2. The process of claim 1, wherein the halogenating agent in (a) is hydrogen chloride or a mixture of gaseous hydrogen chloride and an aqueous solution of hydrogen chloride.

3. The process of claim 1, wherein the reaction of the compound of formula (I) with the halogenating agent in (a) is carried out in the presence of a catalyst.

4. The process of claim 3, wherein the catalyst is an organic acid catalyst, an inorganic acid catalyst, or a heterogeneous acid catalyst.

5. The process of claim 4, wherein the catalyst is an organic acid catalyst selected from the group consisting of a carboxylic, a sulfonic, and a phosphoric acid.

6. The process of claim 1, wherein the base in (b) is selected from the group consisting of a hydroxide, a carbonate and a bicarbonate of alkali metal, alkaline earth metal, and a basic ion exchange resin.

7. The process of claim 6, wherein the base in (b) is selected from the group consisting of LiOH, NaOH, KOH, CsOH, RbOH, Mg(OH)2, Ca(OH)2, Sr(OH)2, NH4OH, Ba(OH)2, Na2CO3, $K_2CO_3$, NaHCO3 and KHCO3.

8. The process of claim 1, wherein the reaction of the compound of Formula (III) with carbon dioxide in (c) is carried out in the presence of a catalyst.

9. The process of claim 8, wherein the catalyst is an alkali metal halide salt or quaternary ammonium halide.

10. The process of claim 9, wherein the alkali metal halide salt is selected from NaCl, NaBr, NaI, KCl, KBr and KI, and the quaternary ammonium halide is selected from tetraethylammonium bromide, tetrapropylammonium bromide, tetraethylammonium chloride, and tetraethylammonium iodide.

11. The process of claim 1, wherein the alcohol in (d) is methanol.

12. A process for producing dimethyl carbonate comprising:
    (a) reacting 3-chloropropane-1,2-diol with hydrochloric acid to form 1,3-dichloro-2-propanol and water

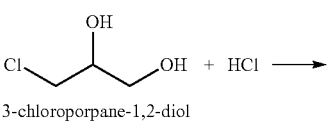

3-chloroporpane-1,2-diol

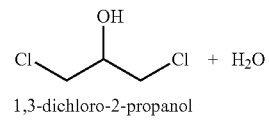

1,3-dichloro-2-propanol (b) reacting 1,3-dichloro-2-propanol with sodium hydroxide in water to form epichlorohydrin, sodium chloride, and water

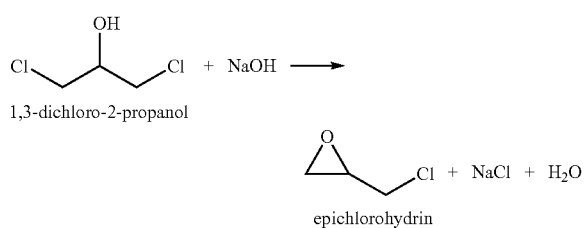

1,3-dichloro-2-propanol epichlorohydrin (c) reacting epichlorohydrin with carbon dioxide in the presence of tetrapropylammonium bromide (TPAB) to form (chloromethyl)ethylene carbonate

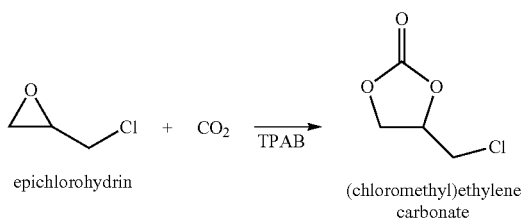

epichlorohydrin     (chloromethyl)ethylene carbonate (d) reacting the (chloromethyl)ethylene carbonate with methanol in the presence of tetrabutyl titanate (TBT) to form dimethyl carbonate and 3-chloropropane-1,2-diol, and

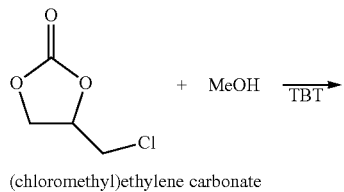

(chloromethyl)ethylene carbonate

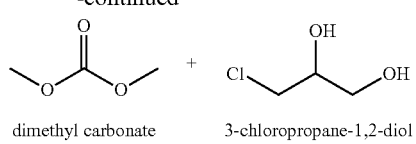

dimethyl carbonate     3-chloropropane-1,2-diol (e) recycling the 3-chloropropane-1,2-diol formed in (d) into (a).

13. The process of claim 12, wherein the reaction of the 3-chloropropane-1,2-diol with hydrochloric acid in (a) is carried out in the presence of a catalyst.

14. The process of claim 13, wherein the catalyst is an organic acid catalyst selected from the group consisting of carboxylic, sulfonic, and phosphoric acids.

15. The process of claim 14, wherein the organic acid catalyst is acetic acid.

16. The process of claim 1, wherein R1 is halide, X is chlorine, R is CH3- group, and the base of step (b) is NaOH.

17. The process of claim 16, wherein the reaction of compound of formula (I) with the halogenating agent, HCl, is carried out in the presence of a catalyst comprising acetic acid.

18. The process of claim 16, wherein the reaction of the compound of Formula (III) with carbon dioxide in step (c) is carried out in the presence of a catalyst comprising tetrapropylammonium bromide.

* * * * *